United States Patent [19]
Goldberg et al.

[11] Patent Number: 5,247,177
[45] Date of Patent: Sep. 21, 1993

[54] DETECTION OF NITROGENOUS MATERIAL

[75] Inventors: Mark Goldberg; David Vartsky; Gideon Engler, all of Rehovot; Aharon Goldschmidt, Ness Ziona, all of Israel

[73] Assignee: The State of Israel, Atomic Energy Commission, Soreq Nuclear Research Center, Nahal Soreq, Israel

[21] Appl. No.: 909,536

[22] Filed: Jul. 6, 1992

Related U.S. Application Data

[63] Continuation-in-part of Ser. No. 679,667, Apr. 3, 1991, abandoned.

[30] Foreign Application Priority Data

Apr. 9, 1990 [IL] Israel ................................. 94050

[51] Int. Cl.$^5$ ..................... G01N 23/08; H05H 6/00
[52] U.S. Cl. ......................... 250/358.1; 250/359.1; 250/360.1; 250/390.04; 250/390.06; 378/53; 378/57; 378/143; 376/194; 376/195
[58] Field of Search ............... 250/392, 391, 390.06, 250/390.04, 390.02, 358.1, 359.1, 360.1; 378/143, 57, 53; 376/194, 195

[56] References Cited

U.S. PATENT DOCUMENTS

| | | | |
|---|---|---|---|
| 4,941,162 | 7/1990 | Vartsky et al. | 378/3 |
| 5,040,200 | 8/1991 | Ettinger et al. | 378/88 |

FOREIGN PATENT DOCUMENTS 1-159942  6/1989  Japan .................................. 378/143

OTHER PUBLICATIONS

Richard A. Ferrieri, David J. Schlyer, Bruce W. Wieland and Alfred P. Wolf, "On-line Production of $^{13}$N-Nitrogen Gas from a Solid Enriched $^{13}$C-Target and its Application to $^{13}$N-Ammonia Synthesis Using Microwave Radiation." Int. J. Appl. Radiat. Isot., vol. 34, No. 6, (1983), pp. 897-900.

Primary Examiner—Constantine Hannaher
Attorney, Agent, or Firm—Helfgott & Karas

[57] ABSTRACT

Improved method and means for the detection of nitrogenous material or assaying of nitrogenous material in an object on the basis of nuclear resonant attenuation of 9.17 MeV γ-rays. A target in form of one or several $^{13}$C pellets at least 25μ thick, or alternatively in form of a body that bears a composite thin film including at least one $^{13}$C layer not more than 1μ thick and at least one other substance that is capable of generating supplementary γ-radiation for determining the non-resonant component of attenuation, is bombarded with 1.75 MeV protons to produce a source of 9.17 MeV γ-rays. The target is placed on one side of the inspected object and a γ-ray detector or an array of such detectors is placed on the other side and the total and non-resonant attenuation are read and evaluated.

13 Claims, 4 Drawing Sheets

DETECTION OF NITROGENOUS MATERIAL

This application is a continuation in part of U.S. Ser. No. 07/679,667, filed Apr. 3, 1991 now abandoned.

FIELD OF INVENTION

The present invention is in the field of non-invasive imaging of nitrogenous materials by using nuclear resonant absorption of gamma rays and is a further development of the invention for detecting nitrogenous explosives disclosed in our U.S. Pat. No. 4,941,162 which is hereby incorporated by reference and which will be referred to hereinafter as "our previous patent". Examples of other applications of this invention include, inter alia, detection of clandestinely transported narcotics and assaying of protein content in food and living tissue.

BACKGROUND OF THE INVENTION

Our previous patent describes a method for the detection of a nitrogenous explosive material within an object, comprising:

(i) placing on one side of the object a source for 9.17 MeV γ-rays adapted to produce the desired photon flux;

(ii) placing on the opposite side of the object a γ-ray detector or an array of detectors with a nitrogen rich detection medium;

(iii) scanning the object with a γ-ray beam from said source;

(iv) reading from said γ-ray detector or array of detectors the total and the non-resonant attenuations of the incident photon flux; and (v) deriving from said attenuations the net resonant attenuation and the spatial distribution thereof.

The method of our previous patent was based on the discovery made in accordance therewith that nitrogen alone manifests a resonant attenuation upon irradiation with γ-rays having the energy of 9.17 MeV. In practice, the resonant component of attenuation in nitrogen, if present, is superimposed on the non-resonant attenuation which γ-rays undergo in all materials. Experimentally, the two quantities directly determined are the total attenuation (resonant and non-resonant) and the non-resonant attenuation. The net resonant attenuation is then extracted from these two quantities and is indicative of the amount of nitrogen traversed by the γ-rays.

As also mentioned in our previous patent, a typical source of 9.17 MeV photons is $^{13}$C which captures 1.75 MeV protons. This manner of producing the desired 9.17 MeV photons can be described by the following equation:

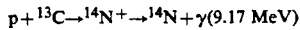

$$p + {}^{13}C \rightarrow {}^{14}N^{+} \rightarrow {}^{14}N + \gamma(9.17 \text{ MeV})$$

For any specific application, this dictates the necessity for an on-site ion accelerator capable of delivering an intense proton beam of well-defined energy and optics to a $^{13}$C-containing target. For example, in the aviation-security/explosives-in-baggage detection scenario, the operational requirement of an inspection time of 6 sec. per bag implies proton beam currents of a few milliamps.

Clearly, the target design must take this factor into account as well as other requirements related to the fundamental features of the gamma attenuation process and the data normalization procedure. The total attenuation is determined by counting the 9.17 MeV resonant component of the photon flux. The non-resonant component is measured by counting photons with energies outside the resonant energy range. The net resonant attenuation is extracted from these two quantities by normalizing the former to the latter and is indicative of the quantity of nitrogen traversed by the γ-rays. In principle, if the normalization is good, the net resonant attenuation will be zero (within counting statistics) for any quantity of all atomic constituents except nitrogen. The two-dimensional radiographic image of net resonant attenuations of the transmission through an inspected object is denoted a "nitrogram". The implications of these methodological features for the targets will be discussed in the following sections.

The present invention is based on some further investigation regarding the desired properties of the high energy photon source for the performance of the method of our previous patent and has for its object the selection of particularly suitable sources therefor.

BRIEF DESCRIPTION OF THE INVENTION

The present invention is based on new findings concerning the sensitivity of the methodology described in our previous patent. These are related to the observation that the practical applicability of nitrogen-specific radiography via Nuclear Resonance Absorption depends critically on the supplementary radiations emitted when target layers, other than those responsible for generating the 9.17 MeV resonant γradiation, are exposed to the proton beam.

Quite generally, for the purpose of nitrogen imaging the 1.75 MeV proton beam must impinge on a target assembly satisfying the following criteria:

(a) it must contain a $^{13}$C layer or layers thick enough to integrate the proton capture resonance yield over all proton energies present in the beam;

(b) it must present other constituents or layers to the beam, the bombardment of which will give rise to non-resonant high energy photon flux. This flux must be sufficiently intense to permit determination of the non-resonant component of attenuation in each pixel through the inspected object, concomitantly with the total (resonant nuclear + non-resonant) attenuation measurement;

(c) the non-resonant flux in (b) must be different enough in energy from 9.17 MeV to be adequately distinguished by the detection system from the resonant flux;

(d) the flux in (b), (c) must be close enough in energy to 9.17 MeV to represent faithfully the non-resonant component of attenuation at the resonant energy for absorbers of any atomic number and quantity which may be present in the inspected object;

(e) satisfactory time stability of all target constituents and components under sustained bombardment with milliamps of protons.

The most obvious and straightforward target to use is a thin layer of isotopically enriched $^{13}$C, evaporated on a thick, water-cooled copper block. It was found that $^{13}$C layers up to about 80 μg/cm$^2$ thick could be made to adhere well to the backing and sustain prolonged proton bombardment at a total beam power density of up to about 4kW/cm$^2$, provided the copper substrate surface was thoroughly cleaned with acid, organic degreasing agents and plasma discharge immediately prior to vacuum deposition of the $^{13}$C. Such a target delivers the desired 9.17 Mev photon beam at a resonant angle of 81°, but this target does not fulfil criteria (b), (c) above sufficiently well, since the microspectrum of the 9.17 MeV photons does not carry a sufficiently high proportion of non-resonant γ-rays. Thus, in the course of the normalization process which generates the nitrogram, a loss of resonant effect is incurred. The alternative with this target is to take another complete radiogram at an angle different from the resonant 81° angle, but the hardware becomes cumbersome and one is likely to generate image artifacts due to non-identical line integrals of γ-rays traversing the inspected object. Clearly, other approaches and solutions to the target problem are called for.

The present invention addresses this problem via the quality of normalization in the nitrogen-related resonance signal by providing for the performance of the method a $^{13}$C-containing target which upon bombardment with 1.75 MeV protons emits in addition to 9.17 MeV γ-rays also non-resonant γ-rays. It has been found in accordance with the invention that targets comprising $^{13}$C pellets which are at least 25μ thick or, alternatively, consisting of at least one composite thin film not more than 1μ thick, deposited on a suitable carrier body and including at least one $^{13}$C layer and at least one other layer such as, for example a fluoride layer, are suitable for generating quantitative, sensitive and artefact-free nitrogen data and images ("nitrograms"). The following brief explanation of the basic physical process underlying the generation of γ-rays when protons impinge on diverse targets will be helpful in understanding the improvement provided in accordance with the present invention.

Protons incident on any target lose energy continuously along their path until they come to rest if the target is thick enough. Thus, the thickness of a target can be defined according to the energy lost in the material. A "thin" $^{13}$C target, in the present context, can be defined as the layer of minimal thickness which ensures that every impinging proton in the beam passes through the resonant energy of 1.746 MeV, at which the nuclear capture reaction giving rise to 9.17 MeV resonant γ-rays takes place. This thickness is mainly governed by the energy spread in the incident beam and is typically a fraction of 1μ. Correspondingly, a "thick" target is a $^{13}$C layer sufficient to stop protons of 1.75 MeV incident energy (e.g. 25-30μ).

As stated above, high energy γ-rays supplementary to the 9.17 MeV resonant radiation are required for normalization purposes. With "thin" targets, these can be generated by presenting layers of other materials to the beam, e.g. fluorine-containing materials. In "thick" targets, the protons produce capture γ-rays at energies intermediate between 9.17 and 7.55 MeV, which serve the same purpose. In all cases the γ-rays are produced by nuclear reactions of one kind or another.

In accordance with the present invention there is provided a method for the detection of nitrogenous material or assaying of nitrogenous concentration within an object, comprising:

(i) placing on one side of the object a target containing $^{13}$C for bombardment with 1.75 MeV protons to produce a source of 9.17 MeV γ-rays;

(ii) placing on the opposite side of the object a γ-ray detector or array of detectors with a nitrogen rich detection medium;

(iii) scanning the object with a γ-ray beam from said source;

(iv) reading from said γ-ray detector or array of detectors the total and the non-resonant attenuations of the incident photon flux; and (v) deriving from said attenuations the net resonant attenuation and the spatial distribution thereof;

characterized in that the said target is a member of the group consisting of $^{13}$C pellets at least 25μ thick and bodies bearing at least one composite thin film being not more than 1μ thick and including at least one $^{13}$C layer and at least one other layer, said at least one other layer containing a substance that is capable of generating supplementary γ-radiation for determining the non-resonant component of attenuation.

Examples of substances capable of generating supplementary γ-radiation are fluorine containing compounds, e.g. fluorides such as, for example, calcium fluoride ($CaF_2$) and barium fluoride ($BaF_2$).

Typically, the thickness of said at least one composite film is a fraction of one μ.

The $^{13}$C pellets used as targets in accordance with the present invention may, if desired, comprise an additional substance capable of generating γ-radiation for determining the non-resonant component attenuation, e.g. $CaF_2$ or $BaF_2$.

The invention further provides for use as targets in the performance of the above method, a member of the group consisting of $^{13}$C pellets at least 25μ thick and bodies carrying at least one composite thin film being not more than 1μ thick and including at least one $^{13}$C layer and at least one other layer, said at least one other layer containing a substance capable of generating supplementary γ-radiation for determining the non-resonant component of attenuation.

The substance capable of generating supplementary γ-radiation may, for example be a fluorine-containing substance such as calcium fluoride ($CaF_2$) or barium fluoride ($BaF_2$).

It has been found in accordance with the present invention that use of any of the above described kinds of targets selected in accordance with the invention satisfies the requirements under (b), (c), (d) and (e) above. The properties of these targets will now be described more specifically.

$^{13}$C Pellet Targets

Measurements performed with $^{13}$C pellet targets were found to exhibit the integral yield of all nuclear reactions of proton+$^{13}$C from the initial bombarding energy down to zero, since the protons slow down and come to rest in the target itself. It was found that the gamma rays emanate exclusively from resonances in the proton capture reaction at different beam energies. When bombarding the pellet at an energy just above the 1.75 MeV resonance, the following radiations were observed with sodium iodide scintillators and lithium-drifted germanium detectors:

| Photon energy | Relative intensity |
| --- | --- |
| 9.17 MeV | 1.0 |
| 8.06 MeV | 0.57 |
| continuum γ-rays from 7.5-9 MeV | 0.35 |

It was shown that this kind of target manifests the required stability under sustained bombardment with high intensity proton beams which is due to the fact that graphite is a rather good heat conductor and has low vapour pressure up to very high temperatures.

Typical pellets are cylinders with dimensions of 1 cm diameter and 0.5 mm thickness.

Further measurements conducted with this kind of target showed the following:

(i) Neither the 8.06 MeV radiation nor the continuum γ-rays exhibit resonant interactions with nitrogenous objects or detectors. Thus, resonant interactions are uniquely associated with the 9.17 MeV resonant radiation and a nitrogen imaging measurement or system based thereupon will not exhibit loss of contrast sensitivity on the nitrogram, compared to targets incorporating thin $^{13}$C layers.

(ii) Normalizing photoprotons to 9.17+8.06 MeV+continuum yields the right value for the net resonant attenuation of a calibrated melamine (66.7% N) absorber, thereby factoring out the non-resonant attenuation component correctly. The fact that the gamma energies are close to 9.17 MeV also augurs well for absence of normalization artefacts by absorbers of medium and high Z.

Targets Being Bodies Bearing Composite Films of $^{13}$C Layers and Fluorine-Containing Substance Layers Likewise, the composite $^{13}$C-fluoride, e.g. $^{13}$C-CaF$_2$ targets, were found to satisfy the above requirements (b) to (e). In specific tests CaF$_2$ and $^{13}$C layers were sequentially vacuum-deposited (in either order) on water-cooled copper blocks by techniques known per se. The fluoride layer was made thick enough ($\sim 10$ μg/cm$^2$) to ensure that the $^{16}$O γ-rays produced in the nuclear reaction

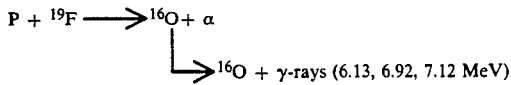

will dominate the high energy photon flux (over the 9.17 MeV radiation). Under these conditions, criteria (a), (b), (c) are well fulfilled for every conceivable detector variant, including non-resonant detectors. Criterion (d) is tolerably well fulfilled, except that concentrations of high-Z substances (e.g. lumps of lead) may appear to look like nitrogen in the nitrogram. With respect to (e), the targets withstood over 10 hours of bombardment with a 200 μA proton beam, but thereafter, deterioration of the $^{13}$C layer set in.

DESCRIPTION OF THE DRAWINGS

In the following some specific embodiments of the invention will be described, by way of example only, with reference to the annexed drawings in which.

DESCRIPTION OF SPECIFIC EMBODIMENTS

Figure 1:
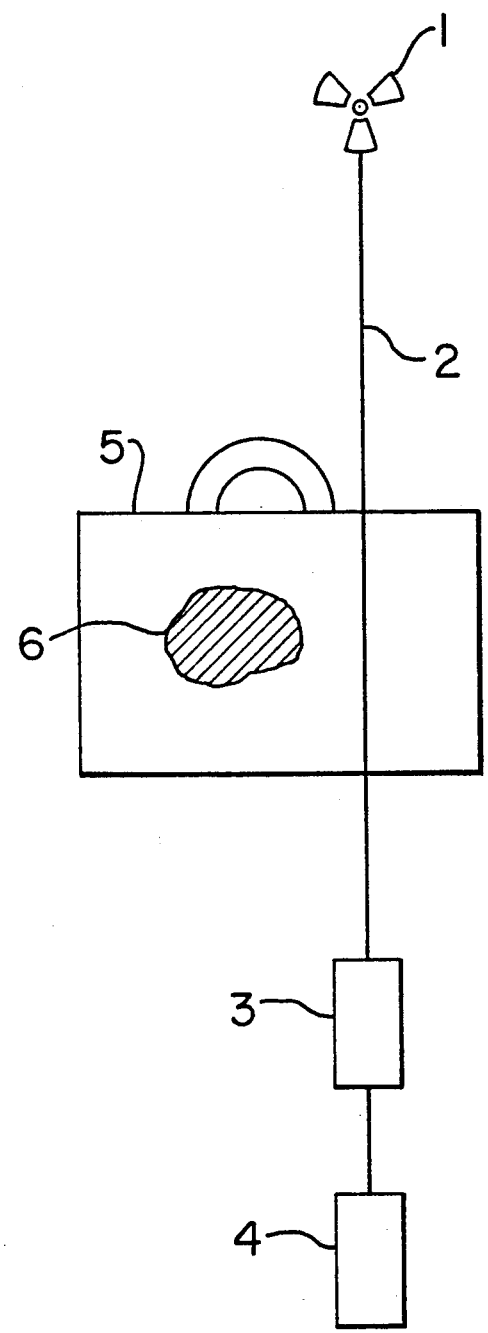
FIG. 1 is a diagrammatic illustration of a system according to the invention.

The method according to the invention is best explained with reference to FIG. 1. As shown, a γ-ray source 1 selected in accordance with the invention emits γ-rays of a desired and monitored flux, symbolized by line 2, so as to impinge on a γ-ray detector 3 electrically linked to a recorder 4. Detector 3 is designed to produce electric signals in response to incident γ-rays and any current modulations are recorded and displayed by recorder 4.

An object 5 held by means of suitable holder means (not shown) is successively moved across beam 2. The object 5 is shown to contain a nitrogenous body 6. As long as body 6 does not intersect beam 2 the γ-rays pass across the object without any resonant attenuation. Once however, body 6 crosses beam 2 the resonant flux detected by detector 3 is attenuated and the information is transmitted to recorder 4.

In the performance of the method according to the invention the object 5 is gradually passed across beam 2 so as to be scanned thereby. This may be achieved either by moving the object itself or else by synchronically moving emitter 1 and detector 3.

Figure 2A:
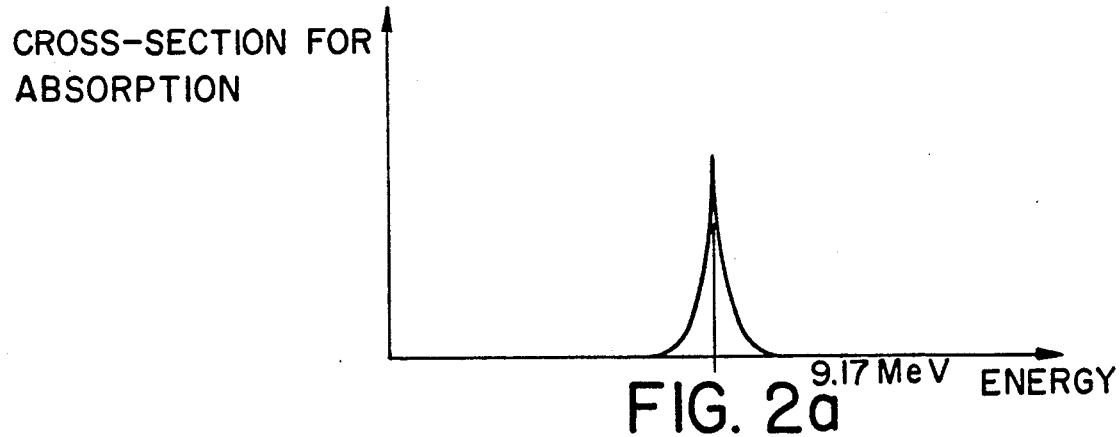
FIGS. 2a–2d are graphical representations in which the cross-section for absorption, incident flux, transmitted flux and detection efficiency are plotted against energy.
Figure 2B:
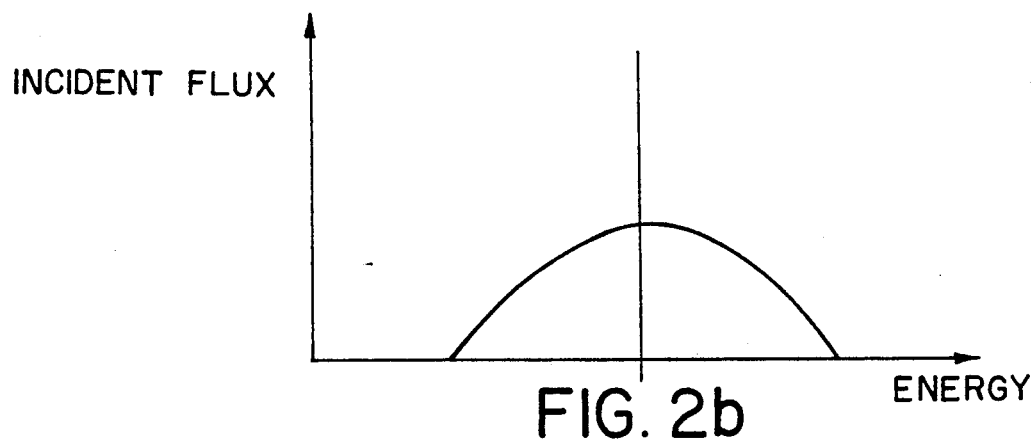
Figure 2C:
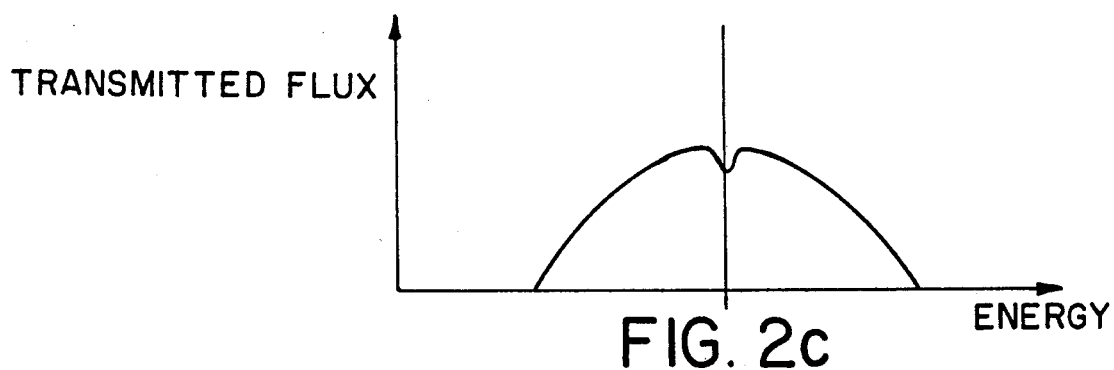
Figure 2D:
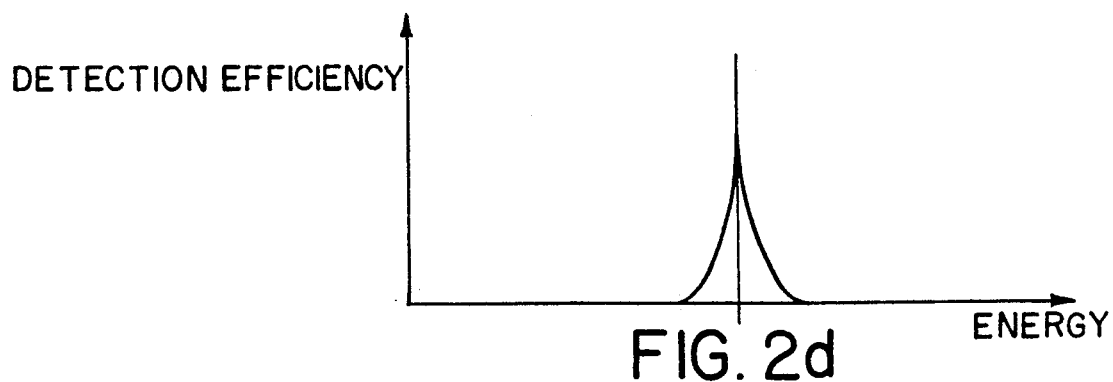

The cross-section for absorption of a photon by a nitrogenous absorber such as a nitrogenous explosive has a resonance shape at 9.17 MeV as shown in FIG. 2a which plots the cross-section for absorption against energy. In FIG. 2b the incident flux is plotted against energy and in FIG. 2c the transmitted flux is plotted against energy. From these two figures it is readily seen that the portion of incident photon flux in the specific energy interval corresponding to the 9.17 MeV excited state will undergo nuclear resonant absorption whenever the beam encounters a region of high nitrogen concentration in the inspected object. This effect can be quantitatively measured by means of an appropriate detector with a resonant response as specified above and as shown in FIG. 2d which plots the detection efficiency against energy. The detection efficiency which is at its peak in the 9.17 MeV range, drops rapidly to zero on both sides.

As explained in our previous patent, nuclear resonant attenuation requires resonant detectors to select the relevant energy portion of the transmitted flux spectrum which contains the resonant absorption information, and the γ-ray detectors with nitrogen rich detection medium fulfil that function. Since, however, in addition to the resonant attenuation there also occurs a conventional non-resonant attenuation, non-resonant detectors, e.g. NaI, Bismuth Germanate detectors or liquid scintillators, are required in order to factor-out this component in the spectrum which is then used for normalization purposes.

Figure 3:
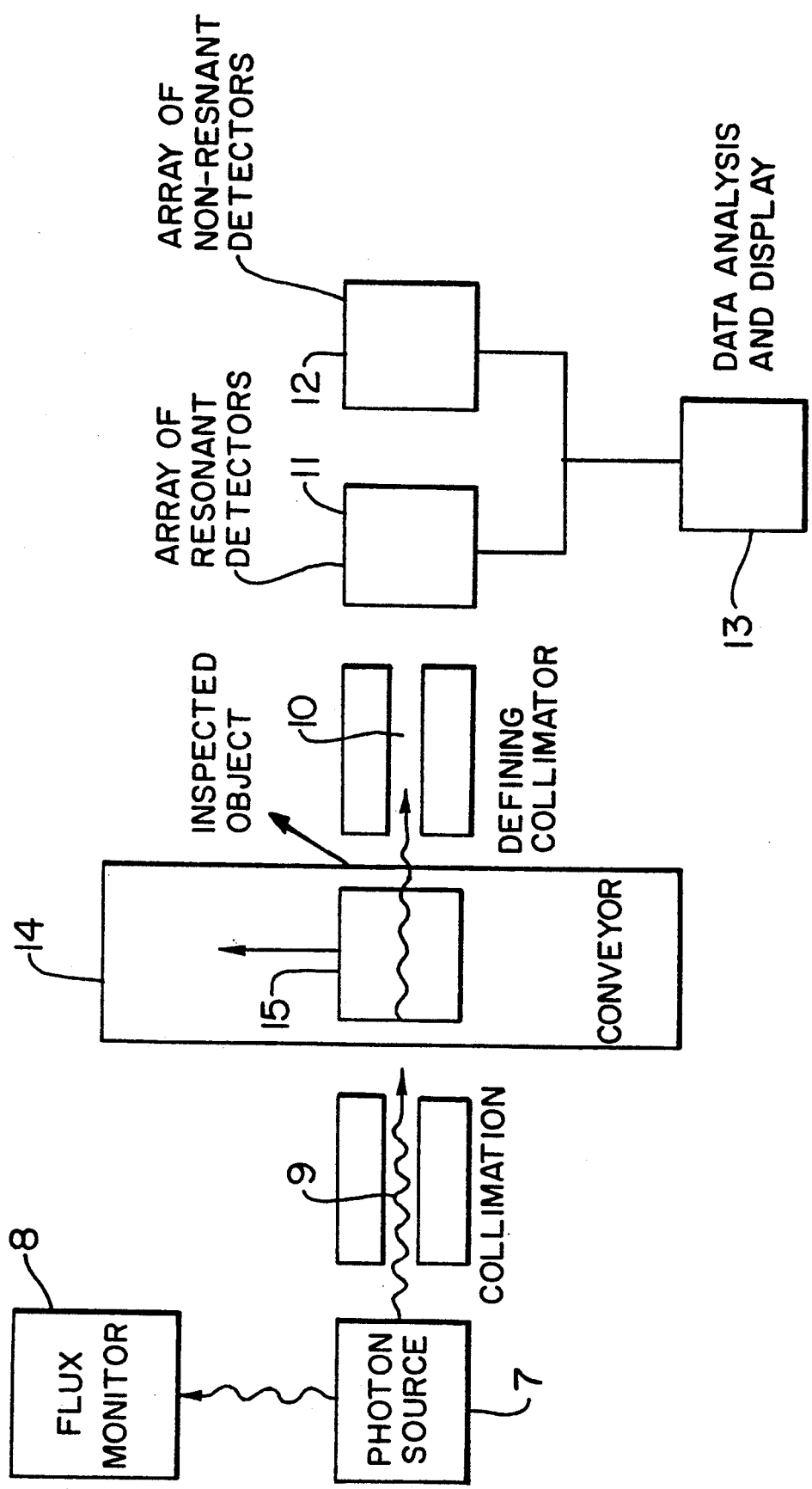
FIG. 3 is a block diagram of a system according to the invention.

FIG. 3 shows a block diagram of an installation according to the invention with resonant and non-resonant detectors. As shown, the system comprises a γ-ray emitter 7 serving as photon source and linked to a flux monitor 8. There are further provided collimator blocks 9 and 10 for the collimation of the γ-radiation emitted from source 7 in front of and behind the inspected object. The system further comprises an array 11 of resonant detectors and an array 12 of non-resonant detectors, both linked to a data analysis and display device 13 which is also linked to the flux monitor in a manner not shown.

The system is associated with a conveyor 14 adapted to move successively a plurality of objects such as object 15 across the beam emitted by photon source 7. After its encounter with an object 15 the passing radiation is once more collimated by collimator lens 10 and is thereupon analysed by the assembly of resonant detectors 11, non-resonant detectors 12 and data analysis devices 13.

Figure 4:
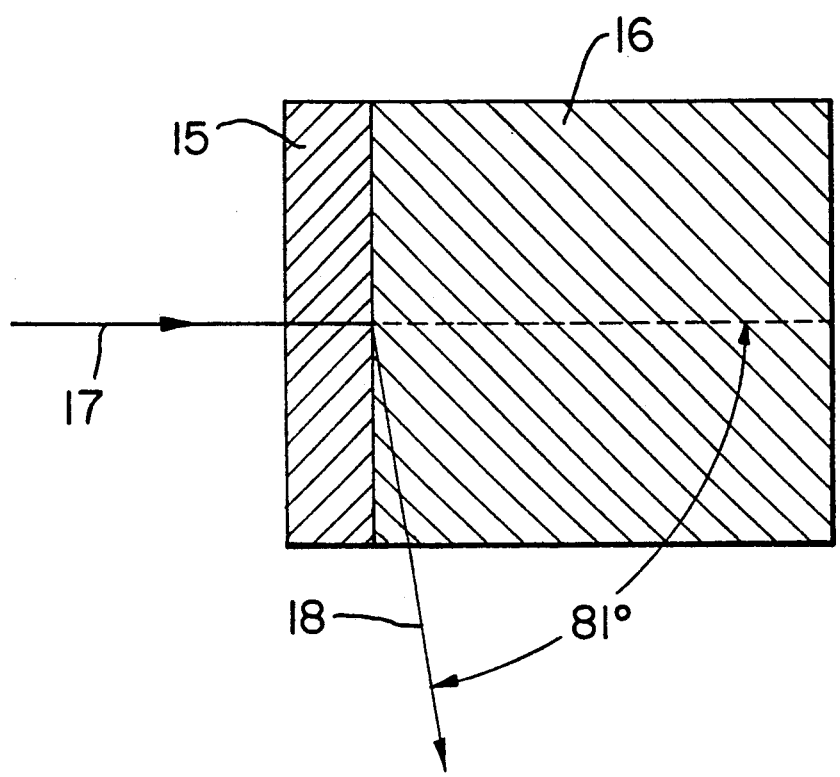
FIG. 4 is a schematic diagram of a backed target according to the invention.

Attention is now directed to FIG. 4 which shows in a schematic fashion a diagram of a backed target according to the invention. As shown, the structure comprises a $^{13}$C-containing target assembly which may consist of $^{13}$C pellets, a composite thin film structure, all as specified and described herein. The $^{13}$C-containing target assembly 15 is mounted on a water-cooled backing-/holder 16. In operation the target assembly 15 is bombarded with a 1.75 MeV proton beam 17 and the desired 9.17 MeV photons required for resonant attenuation by nitrogen are emitted from target assembly 15 in the direction of arrow 18 which forms with the virtual prolongation of beam 17 a polar angle of 81° which is the so-called resonant angle for 9.17 MeV photons. The supplementary radiation needed to satisfy (b) specified herein before is emitted at all angles with respect to the virtual extension of beam 17, but its measurement is performed at the resonant angle.

We claim:

1. A method for the detection of nitrogenous materials or assaying of nitrogenous concentrations within an object, comprising:
   (i) placing on one side of the object a target containing $^{13}$C for bombardment with 1.75 MeV protons to produce a source of 9.17 MeV γ-rays;
   (ii) placing on the opposite side of the object a γ-ray detector or array of detectors with a nitrogen rich detection medium;
   (iii) scanning the object with γ-ray beam from said source;
   (iv) reading from said γ-ray detector or array of detectors the total and the non-resonant attenuations of the incident photon flux; and
   (v) deriving from said attenuations the net resonant attenuation and the spatial distribution thereof;
   characterized in that the said target is a member of the group consisting of $^{13}$C pellets at least 25μ thick and bodies bearing at least one composite thin film being not more than 1μ thick and including at least one $^{13}$C layer and at least one other layer, said at least one other layer containing a substance that is capable of generating supplementary γ-radiation for determining the non-resonant component of attenuation.

2. A method according to claim 1, wherein the target consists of $^{13}$C pellets as defined in claim 1 and said $^{13}$C pellets in said target comprise an additional substance capable of generating γ-radiation for determining the non-resonant component of attenuation.

3. A method according to claim 2, wherein said additional substance is a fluoride.

4. A method according to claim 3, wherein said fluoride is calcium fluoride or barium fluoride.

5. A method according to claim 1, wherein the target consists of a body bearing at least one composite thin film as defined in claim 1 and the substance in the said at least one other layer is a fluoride.

6. A method according to claim 5, wherein said fluoride is calcium fluoride or barium fluoride.

7. $^{13}$C pellets which are at least 25μ thick for use as targets for bombardment with 1.75 MeV protons for the generation of 9.17 MeV γ-rays and supplementary radiation for determining the non-resonant component of attenuation.

8. $^{13}$C pellets according to claim 7, comprising an additional substance capable of generating γ-radiation for determining the non-resonant component of attenuation.

9. $^{13}$C pellets according to claim 8, wherein said additional substance is a fluoride.

10. $^{13}$C pellets according to claim 9, wherein said fluoride is calcium fluoride or barium fluoride.

11. A target for bombardment with 1.75 MeV protons for the generation of 9.17 MeV γ-rays, comprising a body bearing a composite thin film not more than 1μ thick and including at least one $^{13}$C layer and at least one other layer containing a substance capable of generating supplementary radiation for determining the non-resonant component of attenuation.

12. A body according to claim 11, wherein the substance in said at least one other layer is a fluoride.

13. A body according to claim 12, wherein said fluoride is calcium fluoride or barium fluoride.

* * * * *